(12) United States Patent  
Kuhr et al.

(10) Patent No.: US 8,523,784 B2
(45) Date of Patent: Sep. 3, 2013

(54) ANALYTICAL DEVICE WITH LANCET AND TEST ELEMENT

(75) Inventors: Hans-Juergen Kuhr, Mannheim (DE); Michael Fritz, Buerstadt (DE); Thomas Weiss, Mannheim (DE); Richard Forster, Fensterbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 2212 days.

(21) Appl. No.: 10/838,155

(22) Filed: Apr. 30, 2004

(65) Prior Publication Data

US 2005/0021066 A1    Jan. 27, 2005

Related U.S. Application Data

(63) Continuation of application No. 10/230,851, filed on Aug. 29, 2002, now Pat. No. 7,396,334.

(30) Foreign Application Priority Data

Aug. 29, 2001 (DE) .................................. 101 42 232

(51) Int. Cl.
*A61B 5/00* (2006.01)
*B65D 81/00* (2006.01)
*A61B 17/14* (2006.01)
*A61B 17/32* (2006.01)

(52) U.S. Cl.
USPC ........... 600/583; 600/575; 600/576; 606/181; 606/182; 606/183

(58) Field of Classification Search
USPC ................. 600/575, 576, 578, 580, 581, 583; 606/181, 182, 183; 604/6.12, 6.15
See application file for complete search history.

(56) References Cited

U.S. PATENT DOCUMENTS 2,714,890 A    8/1955    Vang
3,030,959 A    4/1962    Grunert
(Continued)

FOREIGN PATENT DOCUMENTS

DE    1 079 275    4/1960
DE    2 131 297    6/1971
(Continued)

OTHER PUBLICATIONS

Surelets Stick It to the Competition/Surelet Blood Lancets . . . In a Class by Themselves, Product Brochure, Gainor Medical, Long Beach, California, USA.

(Continued)

*Primary Examiner* — Sean Dougherty
*Assistant Examiner* — Devin Henson
(74) *Attorney, Agent, or Firm* — Woodard, Emhardt, Moriarty, McNett & Henry LLP

(57) ABSTRACT

The invention concerns an analytical device containing a lancet comprising a lancet needle and a lancet body, the lancet needle being movable relative to the lancet body and the lancet body being composed, at least in the area of the tip of the lancet needle, of an elastic material in which the tip of the lancet needle is embedded, and an analytical test element which is permanently connected to the lancet body. In addition the invention concerns an analytical device containing a lancet comprising a lancet needle and a lancet body which is in the form of a hollow body in the area of the tip of the lancet needle and surrounds the tip of the lancet needle, the lancet needle being movable relative to the lancet body and the hollow body being composed at least partially of an elastic material, and an analytical test element which is permanently connected to the lancet body. Finally the invention concerns a process for manufacturing such an analytical device.

19 Claims, 6 Drawing Sheets

(56) References Cited

U.S. PATENT DOCUMENTS

| | | |
|---|---|---|
| 3,208,452 A | 9/1965 | Stern |
| 3,086,288 A | 4/1969 | Balamuth et al. |
| 3,673,475 A | 6/1972 | Britton, Jr. |
| 3,832,776 A | 9/1974 | Sawyer |
| 4,077,406 A | 3/1978 | Sandhage et al. |
| 4,154,228 A | 5/1979 | Feldstein et al. |
| 4,203,446 A | 5/1980 | Hofert et al. |
| 4,223,674 A | 9/1980 | Fluent et al. |
| 4,230,118 A | 10/1980 | Holman et al. |
| 4,356,826 A | 11/1982 | Kubota |
| 4,392,933 A | 7/1983 | Nakamura et al. |
| 4,398,544 A | 8/1983 | Nugent et al. |
| 4,442,836 A | 4/1984 | Meinecke et al. |
| 4,449,529 A | 5/1984 | Burns et al. |
| 4,462,405 A | 7/1984 | Ehrlich |
| 4,518,384 A | 5/1985 | Tarello et al. |
| 4,535,773 A | 8/1985 | Yoon |
| 4,548,201 A | 10/1985 | Yoon |
| 4,553,541 A | 11/1985 | Burns |
| 4,627,445 A | 12/1986 | Garcia et al. |
| 4,635,633 A | 1/1987 | Hufnagle |
| 4,637,403 A | 1/1987 | Garcia et al. |
| 4,653,513 A | 3/1987 | Dombrowski |
| 4,660,570 A | 4/1987 | Dombrowski |
| 4,695,274 A * | 9/1987 | Fox .............................. 604/198 |
| 4,750,489 A | 6/1988 | Berkman et al. |
| 4,787,398 A | 11/1988 | Garcia et al. |
| 4,794,926 A | 1/1989 | Munsch et al. |
| 4,823,806 A | 4/1989 | Bajada |
| 4,883,068 A | 11/1989 | Dechow |
| 4,889,117 A | 12/1989 | Stevens |
| 4,924,879 A | 5/1990 | O'Brien |
| 4,983,178 A | 1/1991 | Schnell |
| 4,995,402 A | 2/1991 | Smith et al. |
| 5,001,054 A | 3/1991 | Wagner |
| 5,029,583 A | 7/1991 | Meserol et al. |
| 5,035,704 A | 7/1991 | Lambert et al. |
| 5,047,044 A | 9/1991 | Smith et al. |
| 5,059,394 A | 10/1991 | Phillips et al. |
| 5,097,810 A | 3/1992 | Fishman et al. |
| 5,122,123 A | 6/1992 | Vaillancourt |
| 5,145,565 A | 9/1992 | Kater et al. |
| 5,152,775 A | 10/1992 | Ruppert |
| 5,188,118 A | 2/1993 | Terwilliger |
| 5,189,751 A | 3/1993 | Giuliani et al. |
| 5,201,324 A | 4/1993 | Swierczek |
| 5,207,699 A | 5/1993 | Coe |
| 5,222,504 A | 6/1993 | Solomon |
| 5,231,993 A | 8/1993 | Haber et al. |
| 5,279,294 A | 1/1994 | Anderson et al. |
| 5,304,192 A | 4/1994 | Crouse |
| 5,312,366 A | 5/1994 | Vailancourt |
| 5,313,969 A | 5/1994 | Hsieh |
| 5,318,583 A | 6/1994 | Rabenau et al. |
| 5,318,584 A | 6/1994 | Lange et al. |
| 5,320,808 A | 6/1994 | Holen et al. |
| 5,360,012 A | 11/1994 | Ebara et al. |
| 5,360,410 A | 11/1994 | Wacks |
| 5,368,047 A | 11/1994 | Suzuki et al. |
| 5,385,571 A * | 1/1995 | Morita ........................... 606/181 |
| 5,395,387 A | 3/1995 | Burns |
| 5,415,169 A | 5/1995 | Siczek et al. |
| 5,423,847 A | 6/1995 | Strong et al. |
| 5,472,427 A | 12/1995 | Rammler |
| 5,474,084 A | 12/1995 | Cunniff |
| 5,510,266 A | 4/1996 | Bonner et al. |
| 5,514,152 A | 5/1996 | Smith |
| 5,529,074 A | 6/1996 | Greenfield |
| 5,554,166 A | 9/1996 | Lange et al. |
| 5,575,403 A | 11/1996 | Charlton et al. |
| 5,593,391 A | 1/1997 | Stanners |
| 5,624,458 A | 4/1997 | Lipscher |
| 5,630,986 A | 5/1997 | Charlton et al. |
| 5,632,410 A | 5/1997 | Moulton et al. |
| 5,636,640 A | 6/1997 | Staehlin |
| 5,657,760 A | 8/1997 | Ying et al. |
| 5,662,127 A | 9/1997 | De Vaughn |
| 5,700,695 A | 12/1997 | Yassinzadeh et al. |
| 5,714,390 A | 2/1998 | Hallowitz et al. |
| 5,720,924 A | 2/1998 | Eikmeier et al. |
| 5,738,244 A | 4/1998 | Charlton et al. |
| RE35,803 E | 5/1998 | Lange et al. |
| 5,758,643 A | 6/1998 | Wong et al. |
| 5,776,157 A | 7/1998 | Thorne et al. |
| 5,779,677 A | 7/1998 | Frezza |
| 5,788,651 A | 8/1998 | Weilandt |
| 5,800,781 A | 9/1998 | Gavin et al. |
| 5,801,057 A | 9/1998 | Smart et al. |
| 5,810,199 A | 9/1998 | Charlton et al. |
| 5,823,973 A | 10/1998 | Racchini et al. |
| 5,829,589 A | 11/1998 | Nguyen et al. |
| 5,830,219 A | 11/1998 | Bird et al. |
| 5,846,490 A | 12/1998 | Yokota et al. |
| 5,854,074 A | 12/1998 | Charlton et al. |
| 5,855,801 A | 1/1999 | Lin et al. |
| 5,860,922 A | 1/1999 | Gordon et al. |
| 5,863,800 A | 1/1999 | Eikmeier et al. |
| 5,871,494 A | 2/1999 | Simons et al. |
| 5,879,311 A | 3/1999 | Duchon et al. |
| 5,880,829 A | 3/1999 | Kauhaniemi et al. |
| 5,885,211 A | 3/1999 | Eppstein et al. |
| 5,891,053 A | 4/1999 | Sesekura |
| 5,916,229 A | 6/1999 | Evans |
| 5,921,963 A | 7/1999 | Erez et al. |
| 5,935,075 A | 8/1999 | Casscells et al. |
| 5,938,679 A | 8/1999 | Freeman et al. |
| 5,951,492 A | 9/1999 | Douglas et al. |
| 5,951,582 A | 9/1999 | Thorne et al. |
| 5,968,063 A | 10/1999 | Chu et al. |
| 5,971,941 A | 10/1999 | Simons et al. |
| 5,989,227 A | 11/1999 | Vetter et al. |
| 5,997,561 A | 12/1999 | Bocker et al. |
| 5,997,817 A | 12/1999 | Crismore et al. |
| 6,014,577 A | 1/2000 | Henning et al. |
| 6,022,324 A | 2/2000 | Skinner |
| 6,027,459 A | 2/2000 | Shain et al. |
| 6,032,059 A | 2/2000 | Henning et al. |
| 6,036,924 A * | 3/2000 | Simons et al. ................ 600/583 |
| 6,048,352 A | 4/2000 | Douglas et al. |
| 6,056,701 A | 5/2000 | Duchon et al. |
| 6,071,294 A | 6/2000 | Simons et al. |
| 6,090,078 A | 7/2000 | Erskine |
| 6,093,156 A | 7/2000 | Cunningham et al. |
| 6,099,484 A | 8/2000 | Douglas et al. |
| 6,117,630 A | 9/2000 | Reber et al. |
| 6,120,462 A | 9/2000 | Hibner et al. |
| 6,120,676 A | 9/2000 | Heller et al. |
| 6,132,449 A | 10/2000 | Lum et al. |
| 6,136,013 A | 10/2000 | Marshall et al. |
| 6,139,562 A | 10/2000 | Mauze et al. |
| 6,143,164 A * | 11/2000 | Heller et al. .................. 600/583 |
| 6,152,942 A | 11/2000 | Brenneman et al. |
| 6,155,992 A | 12/2000 | Henning et al. |
| 6,156,051 A | 12/2000 | Schraga |
| 6,159,424 A | 12/2000 | Kauhaniemi et al. |
| 6,171,325 B1 | 1/2001 | Mauze et al. |
| 6,176,865 B1 | 1/2001 | Mauze et al. |
| 6,183,489 B1 | 2/2001 | Douglas et al. |
| 6,193,673 B1 | 2/2001 | Viola et al. |
| 6,203,504 B1 | 3/2001 | Latterell et al. |
| 6,206,841 B1 | 3/2001 | Cunningham et al. |
| 6,210,420 B1 | 4/2001 | Mauze et al. |
| 6,210,421 B1 | 4/2001 | Bocker et al. |
| 6,228,100 B1 | 5/2001 | Schraga |
| 6,231,531 B1 | 5/2001 | Lum et al. |
| 6,261,241 B1 | 7/2001 | Burbank et al. |
| 6,261,245 B1 | 7/2001 | Kawai et al. |
| 6,283,926 B1 | 9/2001 | Cunningham et al. |
| 6,285,454 B1 | 9/2001 | Douglas et al. |
| 6,306,104 B1 | 10/2001 | Cunningham et al. |
| 6,306,152 B1 | 10/2001 | Verdonk et al. |
| 6,315,738 B1 | 11/2001 | Nishikawa et al. |
| 6,319,210 B1 | 11/2001 | Douglas et al. |
| 6,332,871 B1 | 12/2001 | Douglas et al. |

| | | |
|---|---|---|
| 6,352,514 B1 | 3/2002 | Douglas et al. |
| 6,358,265 B1 | 3/2002 | Thorne, Jr. et al. |
| 6,364,889 B1 | 4/2002 | Kheiri et al. |
| 6,364,890 B1 | 4/2002 | Lum et al. |
| 6,375,627 B1 | 4/2002 | Mauze et al. |
| 6,379,317 B1 | 4/2002 | Kintzig et al. |
| 6,379,969 B1 | 4/2002 | Mauze et al. |
| 6,391,005 B1 | 5/2002 | Lum et al. |
| 6,402,701 B1 | 6/2002 | Kaplan et al. |
| 6,402,704 B1 | 6/2002 | McMorrow |
| 6,409,740 B1 | 6/2002 | Kuhr et al. |
| 6,416,499 B2 | 7/2002 | Paul, Jr. |
| 6,447,482 B1 | 9/2002 | Rønborg |
| 6,461,496 B1 | 10/2002 | Feldman et al. |
| 6,472,220 B1 | 10/2002 | Simons et al. |
| 6,485,439 B1 | 11/2002 | Roe et al. |
| 6,488,891 B2 | 12/2002 | Mason et al. |
| 6,491,709 B2 | 12/2002 | Sharma et al. |
| 6,497,845 B1 | 12/2002 | Sacherer |
| 6,503,210 B1 | 1/2003 | Hirao et al. |
| 6,506,575 B1 | 1/2003 | Knappe et al. |
| 6,530,892 B1 | 3/2003 | Kelly |
| 6,537,257 B1 | 3/2003 | Wien |
| 6,551,494 B1 | 4/2003 | Heller et al. |
| 6,561,989 B2 | 5/2003 | Whitson |
| 6,576,101 B1 | 6/2003 | Heller et al. |
| 6,607,658 B1 | 8/2003 | Heller et al. |
| 6,612,111 B1 | 9/2003 | Hodges et al. |
| 6,616,616 B2 | 9/2003 | Fritz et al. |
| 6,783,502 B2 | 8/2004 | Orloff et al. |
| 7,001,344 B2 | 2/2006 | Freeman et al. |
| 2001/0031931 A1 | 10/2001 | Cunningham et al. |
| 2002/0002344 A1 | 1/2002 | Douglas et al. |
| 2002/0004196 A1 | 1/2002 | Whitson |
| 2002/0052618 A1 | 5/2002 | Haar et al. |
| 2002/0082543 A1 | 6/2002 | Park et al. |
| 2002/0103499 A1 | 8/2002 | Perez et al. |
| 2002/0177761 A1 | 11/2002 | Orloff et al. |
| 2002/0177763 A1 | 11/2002 | Burns et al. |
| 2003/0032681 A1 | 2/2003 | Coronado et al. |
| 2003/0083685 A1 | 5/2003 | Freeman et al. |
| 2003/0083686 A1 | 5/2003 | Freeman et al. |
| 2003/0088191 A1* | 5/2003 | Freeman et al. ............ 600/583 |
| 2003/0144608 A1 | 7/2003 | Kojima et al. |
| 2003/0153939 A1 | 8/2003 | Fritz et al. |
| 2003/0199789 A1 | 10/2003 | Boecker et al. |
| 2003/0199790 A1 | 10/2003 | Boecker et al. |
| 2003/0199791 A1 | 10/2003 | Boecker et al. |
| 2003/0199893 A1 | 10/2003 | Boecker et al. |
| 2003/0199894 A1 | 10/2003 | Boecker et al. |
| 2003/0199896 A1 | 10/2003 | Boecker et al. |
| 2003/0199898 A1 | 10/2003 | Boecker et al. |
| 2003/0199899 A1 | 10/2003 | Boecker et al. |
| 2003/0199900 A1 | 10/2003 | Boecker et al. |
| 2003/0199901 A1 | 10/2003 | Boecker et al. |
| 2003/0199902 A1 | 10/2003 | Boecker et al. |
| 2003/0199904 A1 | 10/2003 | Boecker et al. |
| 2003/0199906 A1 | 10/2003 | Boecker et al. |
| 2003/0199908 A1 | 10/2003 | Boecker et al. |
| 2003/0199909 A1 | 10/2003 | Boecker et al. |
| 2003/0199910 A1 | 10/2003 | Boecker et al. |
| 2003/0199911 A1 | 10/2003 | Boecker et al. |
| 2003/0201194 A1 | 10/2003 | Heller et al. |
| 2003/0211619 A1 | 11/2003 | Olson et al. |
| 2003/0212344 A1 | 11/2003 | Yuzhakov et al. |
| 2003/0233112 A1 | 12/2003 | Alden et al. |
| 2003/0233113 A1 | 12/2003 | Alden et al. |
| 2004/0009100 A1 | 1/2004 | Simons et al. |
| 2004/0034318 A1 | 2/2004 | Fritz et al. |
| 2004/0055898 A1 | 3/2004 | Heller et al. |
| 2004/0087990 A1 | 5/2004 | Boecker et al. |
| 2004/0092842 A1* | 5/2004 | Boecker et al. ............ 600/575 |
| 2004/0092995 A1 | 5/2004 | Boecker et al. |
| 2004/0102803 A1 | 5/2004 | Boecker et al. |
| 2004/0120848 A1 | 6/2004 | Teodorczyk |

FOREIGN PATENT DOCUMENTS

| | | |
|---|---|---|
| DE | 24 61 273 | 12/1974 |
| DE | 28 03 345 B1 | 6/1979 |
| DE | 38 42 317 A1 | 6/1990 |
| DE | 43 20 463 A1 | 12/1994 |
| DE | 100 47 419 A1 | 4/2002 |
| DE | 101 63 646 - | 7/2003 |
| EP | 0 199 484 A2 | 10/1986 |
| EP | 0 359 831 | 3/1990 |
| EP | 0 589 186 A1 | 3/1994 |
| EP | 0 565 970 B1 | 6/1994 |
| EP | 0931507 A1 | 7/1999 |
| EP | 1 466 558 A2 | 8/2002 |
| EP | 1 285 629 A1 | 2/2003 |
| EP | 1 374 770 A1 | 1/2004 |
| FR | 289191 | 11/1953 |
| GB | 1080986 | 8/1967 |
| GB | 2331936 A1 | 6/1999 |
| GB | 2 352 403 | 1/2001 |
| JP | 2001-11275 | 4/1990 |
| JP | 2-326247 | 11/1990 |
| JP | 04194660 A1 | 11/1990 |
| JP | 9-276235 | 10/1997 |
| JP | 10-296325 | 10/1998 |
| JP | 2000-116626 | 4/2000 |
| JP | 2000116768 A2 | 4/2000 |
| WO | WO 93/02720 A1 | 2/1993 |
| WO | WO 93/12726 | 7/1993 |
| WO | WO 94/016737 A1 | 8/1994 |
| WO | 96/02189 A1 | 2/1996 |
| WO | WO 97/42888 | 11/1997 |
| WO | WO 98/14125 | 4/1998 |
| WO | WO 98/35225 A1 | 8/1998 |
| WO | WO 98/48695 | 11/1998 |
| WO | WO 99/29429 | 6/1999 |
| WO | WO 99/26539 | 10/1999 |
| WO | WO 00/40150 | 7/2000 |
| WO | WO 01/00090 A1 | 1/2001 |
| WO | WO 01/34029 A1 | 5/2001 |
| WO | WO 01/66010 A1 | 9/2001 |
| WO | WO 02/056769 A1 | 7/2002 |
| WO | WO 03/088834 A1 | 10/2003 |
| WO | WO 03/088835 A2 | 10/2003 |
| WO | WO 2004/041082 A1 | 5/2004 |

OTHER PUBLICATIONS

Surelite . . . lancets that baby your skin, Packaging and Ordering Information, Gainor Medical, Long Beach, California, USA.

Notice of Opposition to European Application No. 1 466 558 by Abbott Laboratories, Jun. 3, 2009.

DE 1 079 275 English language translation.

Elastizitat, CD Rompp Chemie Lexikon—Version 1.0 with Machine Translation.

Elastomere, CD Rompp Chemie Lexikon—Version 1.0 with Machine Translation.

TPE, CD Rompp Chemie Lexikon—Version 1.0 with Machine Translation.

* cited by examiner

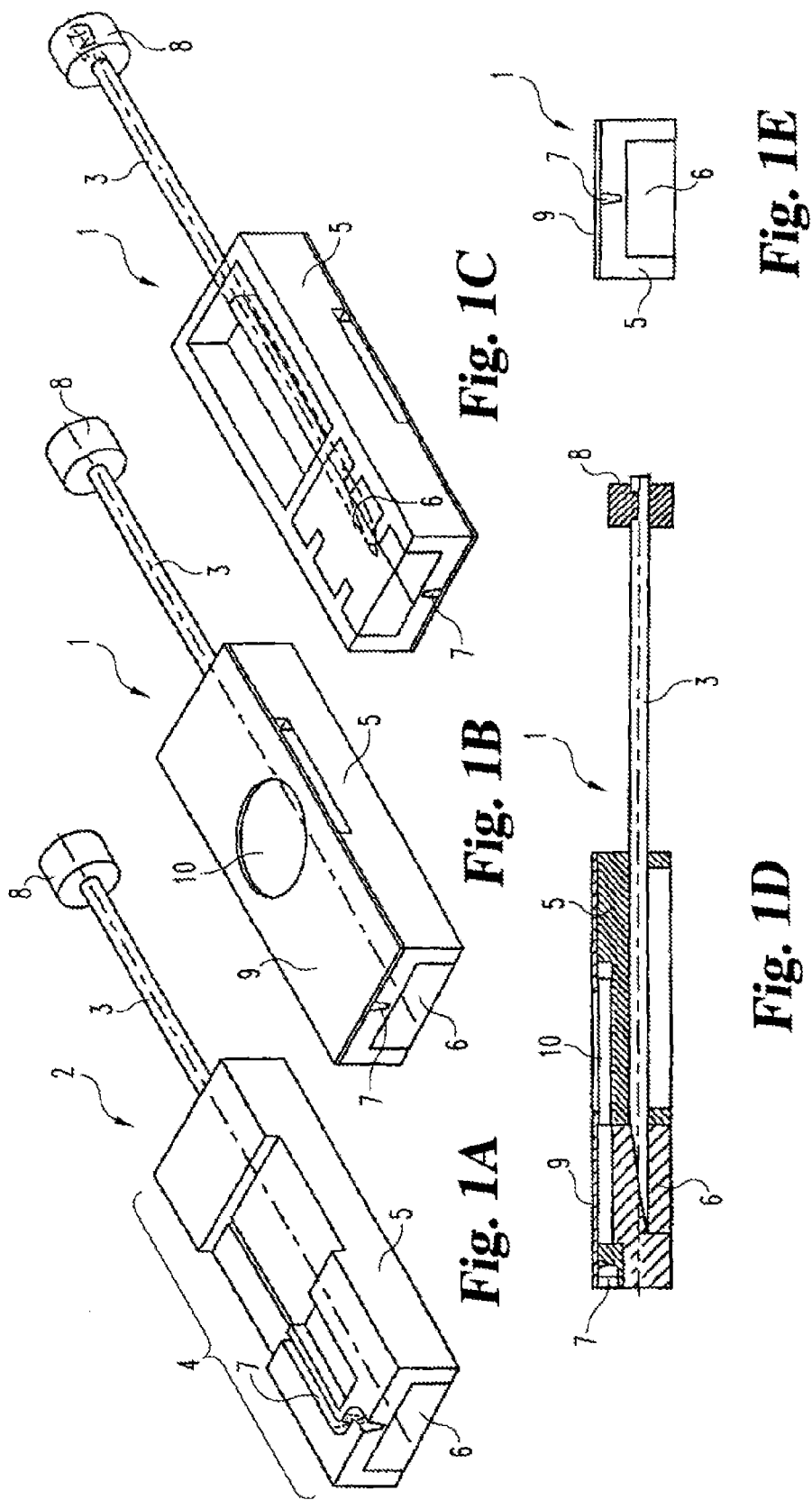

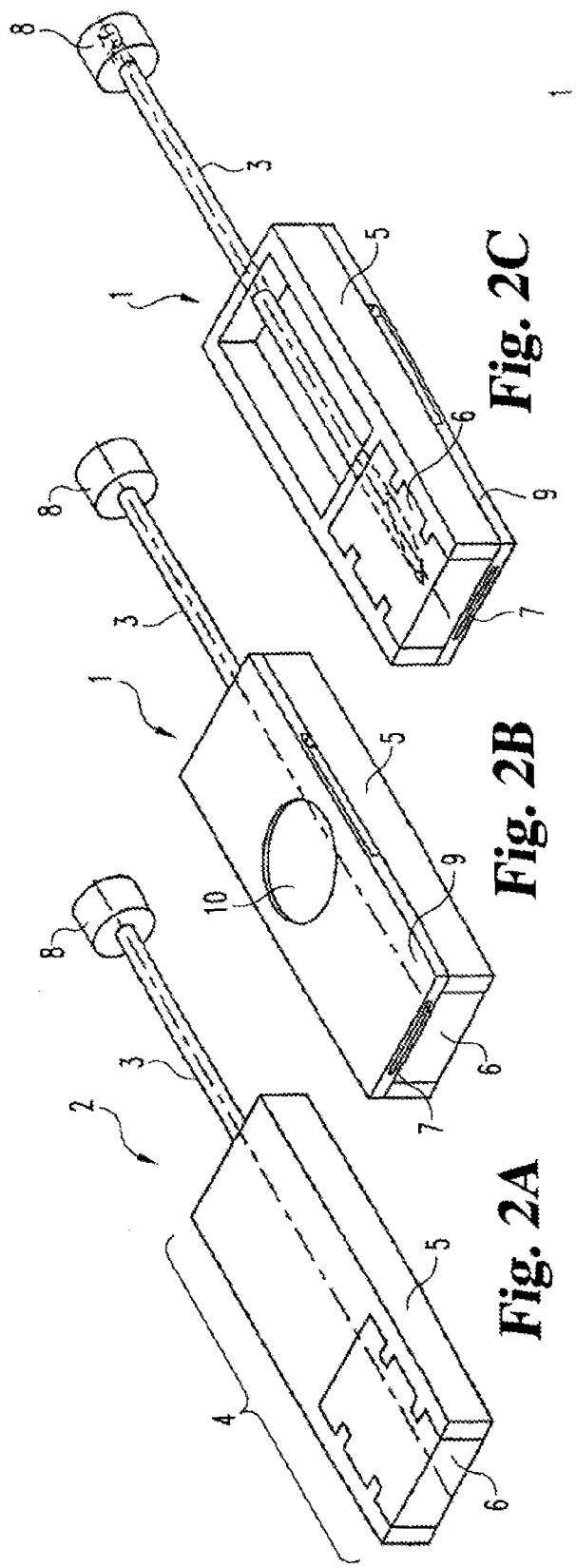
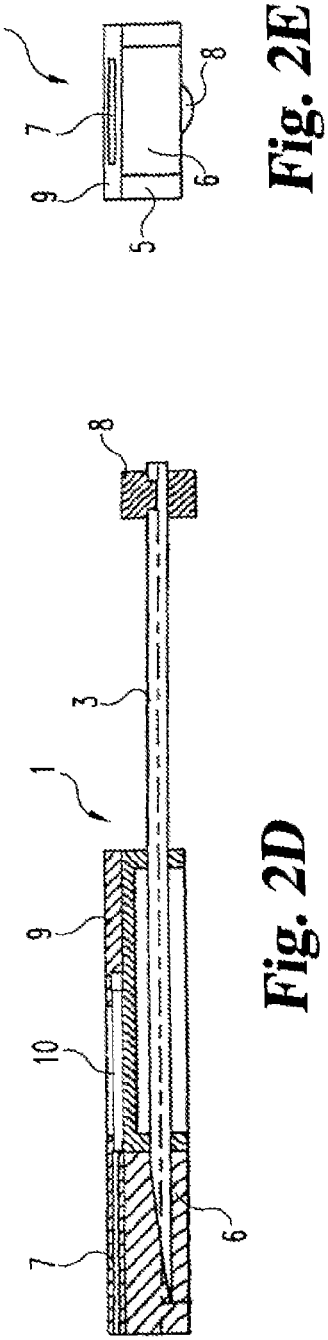
Fig. 2A  Fig. 2B  Fig. 2C  Fig. 2D  Fig. 2E

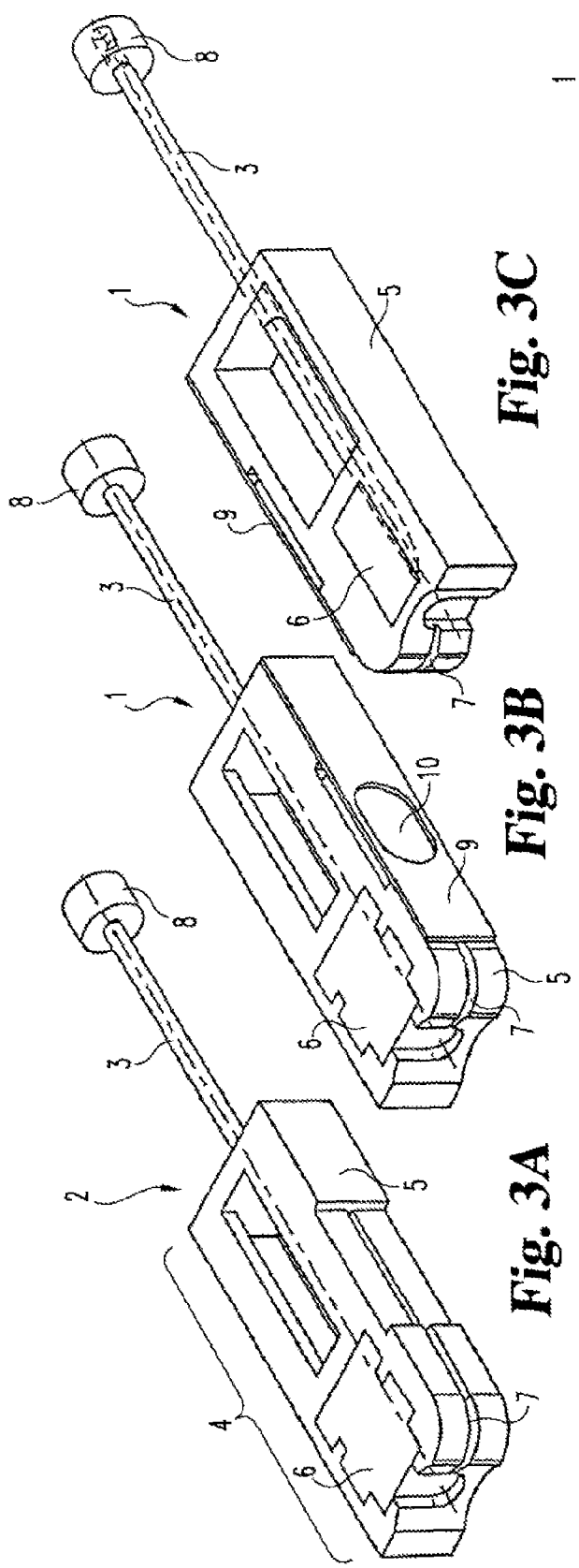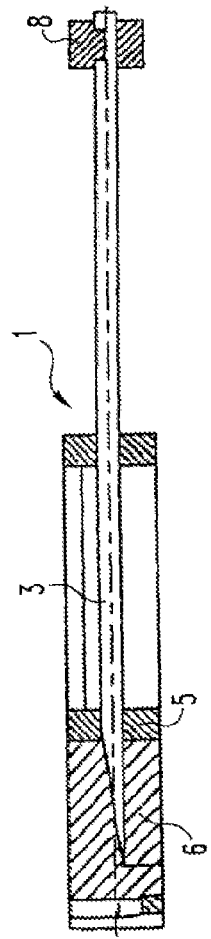

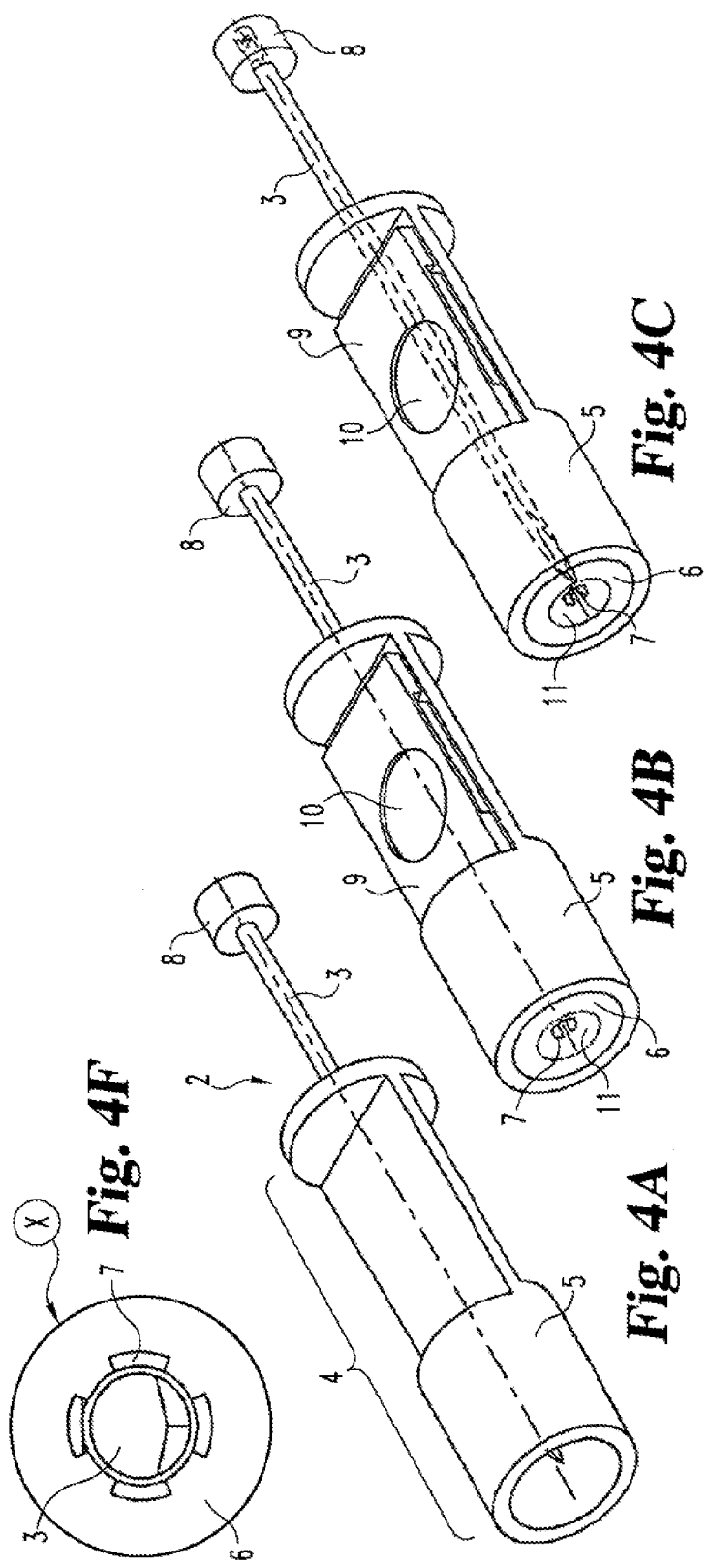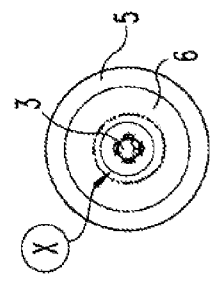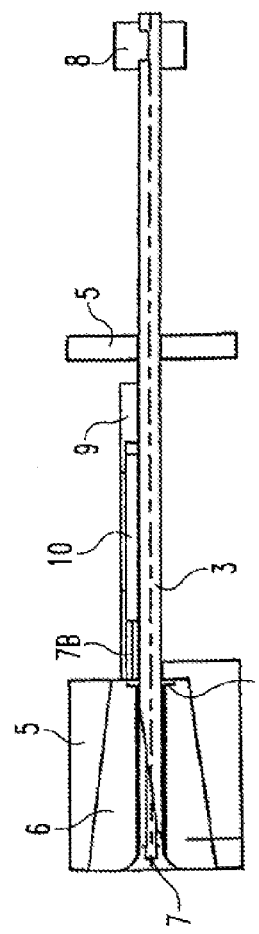

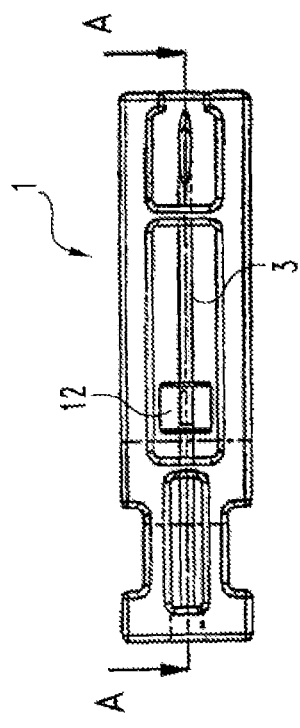
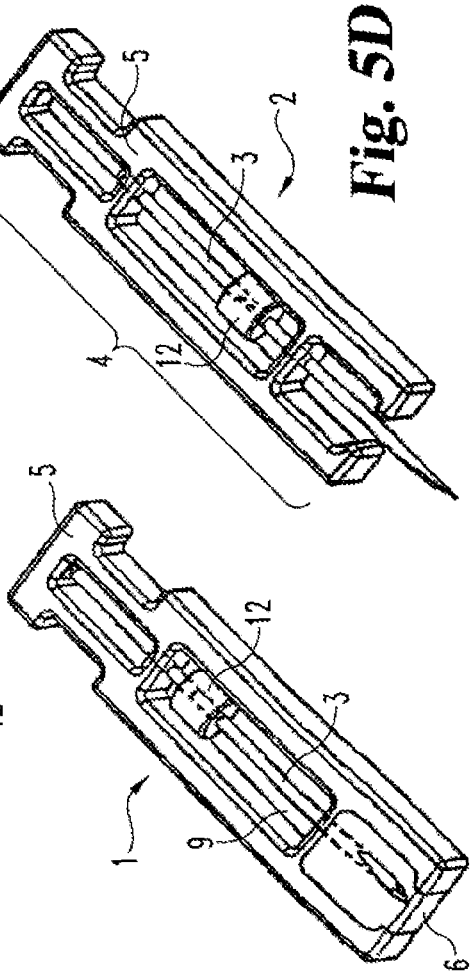
Fig. 5A
Fig. 5B
Fig. 5C
Fig. 5D

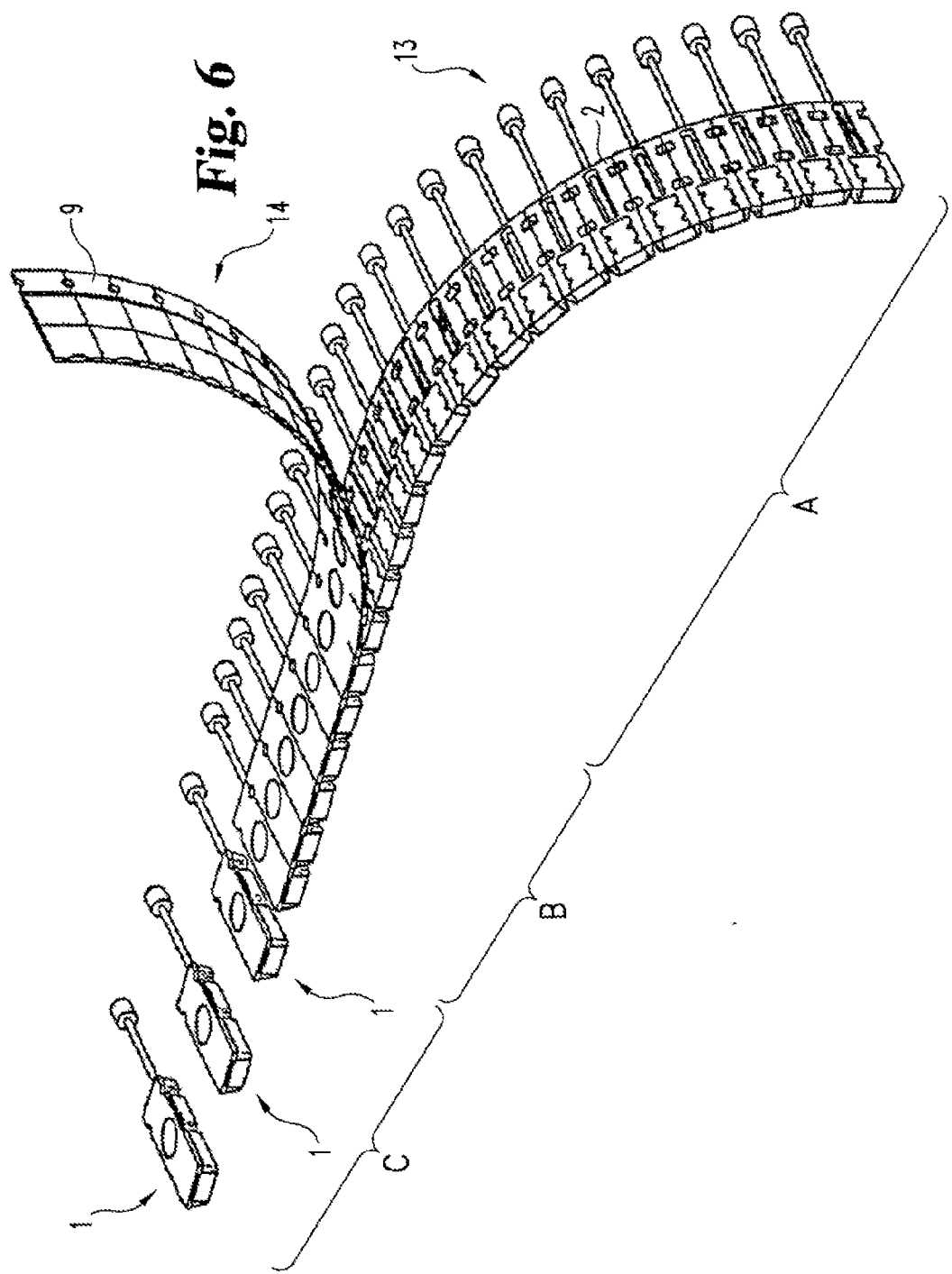

ent) need a lot of space and require a relatively complex handling. There are now also systems with a high degree of integration which are thus more simple to operate. These for example include the AccuCheck Compact (from Roche Diagnostics), the Glucometer Dex (from Bayer Diagnostics) and the Soft-Sense (from Medisense). In the two former systems the test strips are stored in the measuring instrument in magazines and are available for the measurement.

ANALYTICAL DEVICE WITH LANCET AND TEST ELEMENT

REFERENCE TO RELATED APPLICATIONS

The present application is a continuation of U.S. patent application Ser. No. 10/230,851, filed Aug. 29, 2002 which claims priority to German Patent Application No. DE 101 42 232.6, filed Aug. 29, 2001, which are hereby incorporated by reference in their entirety.

BACKGROUND

The invention concerns an analytical device which contains a lancet and an analytical test element. The invention also concerns a process for manufacturing such an analytical device.

The examination of blood samples in clinical diagnostics enables the early and reliable recognition of pathological states as well as a specific and well-founded monitoring of physical conditions. Medical blood diagnostics always requires the collection of a blood sample from the individual to be examined. Whereas in hospitals and in doctor's offices several millilitres of blood are usually collected by venepuncture from a person to be examined for analysis in order to carry out many laboratory tests, individual analyses which are directed towards one parameter nowadays often only require blood quantities ranging from a few microlitres down to less than one microlitre. Such small quantities of blood do not require a laborious and painful venepuncture. Instead it is sufficient to push a sterile sharp lancet into a finger pad or earlobe of the person to be examined to collect blood through the skin and thus to obtain a few microlitres of blood or less for analysis. This method is particularly suitable when it is possible to carry out the analysis of the blood sample immediately after blood collection.

Lancets and suitable instruments for them (so-called blood withdrawal instruments, blood lancet devices or—as they are referred to in the following—lancing aids) which enable blood collection that is as painfree and reproducible as possible are available especially for so-called home monitoring i.e. where medical laymen carry out simple analyses of the blood by themselves and are used in particular by diabetics to collect blood regularly and several times daily to monitor the blood glucose concentration. Furthermore the use of lancets with lancing aids is intended to reduce the psychological barrier associated with piercing one's own body which is particularly important for children that suffer from diabetes and need regular blood glucose tests. The commercially available instruments (lancing aids) and lancets Glucolet® from Bayer AG and Softclix® from Roche Diagnostics GmbH are mentioned as examples of lancets and lancing aids. Such lancets and instruments (lancing aids) are for example the subject matter of WO-A 98/48695, EP-A 0 565 970, U.S. Pat. No. 4,442,836 or U.S. Pat. No. 5,554,166.

Personal blood sugar determination (so-called home monitoring) is today a world-wide method in diabetes monitoring. Blood sugar instruments of the prior art such as the Accu-Chek Sensor (from Roche Diagnostics) are composed of a measuring instrument into which a test element (test strip, sensor) is inserted. The test strip is contacted with a drop of blood which has previously been collected from the finger pad by means of a lancing aid. The numerous system components (lancet, lancing aid, test strip and measuring instrument) need a lot of space and require a relatively complex handling. There are now also systems with a high degree of integration which are thus more simple to operate. These for example include the AccuCheck Compact (from Roche Diagnostics), the Glucometer Dex (from Bayer Diagnostics) and the Soft-Sense (from Medisense). In the two former systems the test strips are stored in the measuring instrument in magazines and are available for the measurement.

A next step in miniaturization is for example to integrate several functions or functional elements into a single analytical device (disposable). For example the operating process can be considerably simplified by a suitable combination of the lancing process and sensory analyte concentration detection on a test strip. There are the following examples of this in the prior art:

EP-B 0 199 484 (Audio Bionics) describes an analytical device ("disposable"; abbreviated dispo) containing an integrated lancet which is actuated by the instrument (see FIG. 9 for example). The lancet is retracted again after the puncture by means of a specific spring mounting ("spring-mounted lance means"). The dispo contains a so-called "wick means" through which the sample liquid is passed from the body surface to the analytical area which is an optically analysable test field.

A method is described in U.S. Pat. No. 6,143,164 (E. Heller & Comp.) in which a body opening (for example a small puncture or incision through the skin) is made and subsequently body fluid is transported into a sensor and examined there for the presence of an analyte. For this purpose U.S. Pat. No. 6,143,164 discloses an analytical device in which a lancing device is attached to a sensor test strip. The sample liquid is transported from the body opening to the actual detection element of the sensor for example again by means of a wick or a capillary gap/channel.

WO 99/26539 (Mercury Diagnostics), U.S. Pat. No. 5,951,492 (Mercury Diagnostics) and U.S. Pat. No. 6,056,701 (Amira Medical) describe, inter alia, collection devices for body fluids comprising an elongate handle; a test field being attached to its head region.

U.S. Pat. No. 6,032,059 (Abbott) and U.S. Pat. No. 6,014,577 (Abbott) describe a disposable containing a needle which is used to pierce the skin. Body fluid which is previously sucked into the needle by capillary action is analysed by a sensor integrated into the needle.

U.S. Pat. No. 5,801,057 (Smart et al.) describes a disposable made of silicon containing an integrated hollow needle. A collection chamber for aspirated body fluid is located at one end of this hollow needle. The concentration of a blood component can be determined in the body fluid by a suitable reaction chemistry.

U.S. Pat. No. 5,035,704 (Lambert et al.) discloses a system for collecting blood containing a magazine for disposables. It is possible to integrate a lancet element into the dispos. A blood drop is transferred to the test field by direct skin contact and can be increased by applying a vacuum.

U.S. Pat. No. 6,132,449 (Agilent Technologies) discloses an integrated dispo with a puncturing and measuring function. The puncturing element is activated perpendicular to the dispo plane whereby it passes through the dispo. The wound opening is in direct contact with several capillary structures which transport the emerging blood into a separate analytical part of the dispo.

A key problem in collecting blood using a so-called "integrated disposable" (in which the lancet and test element are connected together or form a single unit) is the fact that, after puncture, the capillary blood usually does not automatically emerge from the wound. This adverse effect is increased by directly contacting a disposable with the wound opening. After a puncture the blood drop must be actively conveyed to the skin surface by for example mechanically opening the wound and/or applying gentle pressure to the tissue around the wound area (for example by simple "finger milking"). Application of a vacuum can assist this process.

Experiments in the laboratory have shown that it is advantageous to keep the wound open during the period of blood collection. However, this fact results in a complicated movement process of the dispo since a very rapid piercing motion and a slow blood withdrawal movement can only be achieved with a waiting time in the system. Only a few of the dispo designs proposed in the prior art are suitable for this.

A rigid protruding lancet tip has a tendency to cause unintentional injury when collecting the blood drop. Hence a lancing device which moves relative to the disposable is preferable. However, this requirement in combination with the dispos known in the prior art leads to a complicated and thus expensive dispo design.

A further difficulty with known dispos is to ensure the sterility of the lancet for the period until it is used. In the prior art it is known that the tip can be protected by a cap which is manually removed before use. However, such a cap impairs the automation of blood sugar measurements. Previously described concepts which would in principle enable an automated blood sugar determination with an integrated disposable have the disadvantage that there is a latent risk of contaminating the lancet needle tip. Components of the test field (chemicals, biological components, adhesives etc.) can migrate within the dispo via the air or over the surfaces. Thus a sterilization of the needle tip carried out initially is in no way sufficient without further protective measures to meet the requirements for a sterile medical product.

The lancets of the prior art usually have a metal lancet needle with a tip which can be optionally ground. In order to facilitate the handling of the lancet and optionally to attach it in a lancing device, a plastic lancet body made of a rigid, injection-mouldable material is usually injected onto the lancet needle in many embodiments. In the unused state the tip of the lancet needle is surrounded by a protective covering to ensure its sterility. This is usually composed of the same rigid material as the actual lancet body and usually forms one unit with this body. The protective covering can be separated from the lancet body before using the lancet and removed from the tip of the lancet needle. For this purpose there is usually a weakened point between the lancet body and protective cover. After the lancet has been used, the tip of the lancet needle is unprotected and is hence a potential source of injury to the user and possibly to other persons.

The object of the present invention was therefore to eliminate the disadvantages of the prior art and in particular the disadvantages mentioned above. In particular the object of the present invention was to provide analytical devices (synonymous with "disposables", abbreviated: "dispos") which do not have the disadvantages of the prior art. In particular the dispo according to the invention should ensure the sterility of the lancets until they have been used while simultaneously integrating the lancet and test element (test strip, sensor). Of course it is also intended to describe a manufacturing process for such analytical devices. Another object of the present invention is to provide analytical devices containing lancets in which at least the lancet needle tip is kept sterile, i.e. germ-free, in the unused state until immediately before use and which can be stored hygienically in the used state. This object should be ideally achieved without the user having to employ separate measures for the hygienic storage. Moreover the user should be protected from accidental injury by the lancet and in particular by the used lancet. Finally it should be preferably possible to simply transfer the sample from the site of blood collection to the site of blood examination.

This object is achieved by the subject matter of the invention as characterized in the individual patent claims. Preferred embodiments are the subject matter of the dependent claims.

A first subject matter of the invention is an analytical device which contains a lancet. The main components of the lancet are a lancet needle with a tip and a lancet body that completely surrounds the lancet needle at least in the region of the tip. The lancet needle can be moved relative to the lancet body. The lancet body is composed of an elastic material at least in the region of the tip of the lancet needle in which the tip of the lancet needle is embedded. The analytical device additionally contains an analytical test element which is permanently attached to the lancet body.

Another subject matter of the invention is a further analytical device which contains a lancet. The lancet in this case comprises a lancet needle with a tip and a lancet body which is in the form of a hollow body in the region of the tip of the lancet needle and which surrounds the tip of the lancet needle. In this case the lancet needle is also movable relative to the lancet body. The hollow body is composed at least partially of an elastic material which can be pierced by the tip of the lancet needle during the lancing process and after retraction optionally reseals the tip of the lancet needle in the hollow body. The analytical device additionally contains an analytical test element which is permanently connected to the lancet body.

Finally the invention concerns a process for manufacturing such analytical devices.

The object of the invention is preferably composed of a miniaturized dispo which combines the three functions of puncturing, blood transfer from the wound generated by the puncturing to the test element and sensor in one element.

The main body of the analytical device according to the invention is composed of a rigid plastic body whose external shape is preferably adapted for the purpose of holding it in an instrument. A lancet needle is embedded in this plastic in such a manner that its tip preferably does not protrude beyond the front edge of the main body. The main body can therefore also be referred to as the lancet body. In the preferred embodiment the main body has ridges which are used to fix the needle in the main body and to guide it during the lancing movement. However, most of the needle is preferably not attached to the main body in order to reduce the frictional force during the lancing movement. The contact surfaces between the needle and lancet body are preferably kept to a minimum and suitably pretreated, for example siliconized.

The lancets according to the invention are preferably designed to be used once and can therefore be referred to as single-use blood lancets or disposable blood lancets. The lancet of the invention comprises a needle (lancet needle) with a tip. The needle is usually several millimetres (mm) to a few centimetres (cm) in length and has an elongate shape. Needles are typically cylindrical since this needle shape is particularly easy to manufacture; however, other needle shapes are also possible. The tip region of the needle comprises the needle tip which is inserted into the tissue when the lancet is used correctly. Consequently the tip of the lancet needle is that part of the lancet which comes into contact with the skin of the individual to be pricked which optionally injures the skin and thus causes a body fluid and in particular blood or interstitial fluid to flow out.

The tip of the lancet needle can for example be rotationally symmetrical which is generally the case for pins. However, it has also proven to be advantageous to provide the needle tip with one or several ground surfaces. The resulting edges which make an angle with the longitudinal axis of the needle and converge in a tip act as a sharp cutting edge during lancing and make the puncturing process less painful than is the case with rotationally symmetrical needles.

The lancet needle of the lancet according to the invention is manufactured from a material which is sufficiently rigid to withstand mechanical strain during the lancing process, the processing steps or other strains which may occur without deformation. The material must also be such that no particles break off or become detached during the lancing process. Finally the needle material must also be sufficiently machinable to enable the needle tip to be sufficiently pointed and the edges of the needle to be ground adequately sharply. Very suitable materials for the lancet needle are above all metals and in particular high-grade steels. However, needles can also conceivably be made of silicon, ceramics or plastics. High-grade steel needles are particularly preferred.

In one embodiment of the invention at least the tip of the lancet needle of the lancet according to the invention is surrounded by the lancet body. In this connection it is important that the lancet body is composed of an elastic material in the region of the tip of the lancet needle. At least the tip of the lancet needle is completely surrounded on all sides by this elastic material i.e. it is embedded in it and thus sealed from the environment. The elastic material of the lancet body, which in the various embodiments can completely or only partially form the lancet body, is characterized in that it is soft, deformable and can be pierced by the tip of the lancet needle without damaging the tip. During the lancing process the lancet needle is moved along its longitudinal axis relative to the lancet body and its tip emerges from the lancet body in order to pierce the skin of the individual to be examined for blood collection. A further important and preferred property according to the invention is that the elastic material optionally again makes a tight seal around the tip of the lancet needle when the lancet needle is retracted into the lancet body. After the lancing process the lancet needle is moved in a preferred embodiment into its initial position relative to the lancet body by reversing the movement of the lancing process and in this position the tip is again completely enclosed on all sides by the elastic material of the lancet body.

The elastic material of the lancet body which completely encloses the tip of the lancet needle ensures the sterility of the lancet needle tip before use, preferably until immediately before use and optionally ensures a hygienic enclosure of the lancet needle tip after use. The term "hygienic enclosure" means that biological material (tissue, body fluid) which may adhere to the needle after the puncture is essentially encapsulated by the elastic material. This prevents especially germs and infectious material from reaching the environment or at least greatly reduces this risk.

Consequently the elastic material is impervious to germs and thus prevents their penetration or escape depending on whether the lancet needle is unused or used. In addition the elastic material represents a mechanical protection for the lancet needle tip and thus also prevents accidental injury on the lancet needle tip.

Rubber, coautchouc, silicone, elastomers and in particular thermoplastic elastomers have proven to be suitable as an elastic material for the lancet body of the present invention. These have properties that are important for the present invention: they are soft, deformable, can be pierced by the lancet needle without damaging the tip and make a tight seal around the used lancet needle tip. Furthermore they can be used for injection moulding processes which allows a mass production of lancets in large numbers.

Thermoplastic elastomers which are also called elastoplasts or thermoplasts or thermoplastic coautchoucs ideally combine the handling properties of elastomers and the processing properties of thermoplasts. Thermoplastic elastomers are for example styrene oligoblock copolymers (so-called TPE-S), thermoplastic polyolefins (TPE-O), thermoplastic polyurethanes (TPE-U), thermoplastic copolyesters (TPE-E) and thermoplastic copolyamides (TPE-A). In particular thermoplastic elastomers based on styrene-ethylene-butylene-styrene-polymers (SEBS polymers, e.g. Evoprene® from Evode Plastics or Thermolast K from "Gummiwerk Kraiburg GmbH) have for example proven to be particularly suitable.

During the lancing process the lancet needle is moved relative to the lancet body. The latter is preferably held in its position by the lancing aid or lancing instrument during this process. The lancet needle can be specially shaped for the purposes of the drive mechanism and for example have a needle head at the end opposite to the tip or have another lancet body in addition to the lancet body which encloses the tip and can be engaged by a drive element of the lancing aid. The shape of the needle or of the additional lancet body can interact in a suitable manner with a corresponding drive device in the lancing instrument (lancing aid). Such means can generally be referred to as a thickening of the needle.

In order to achieve the advantage that the lancet needle tip is enclosed in a sterile manner before use by the elastic material of the lancet body and is hygienically surrounded by the elastic material after use, it is of course necessary that the lancet needle is moved back after use, i.e. after the lancing process, essentially into its original position relative to the lancet body containing the elastic material. This can be achieved by suitable interaction with a correspondingly adapted lancing aid. It is only important that, after use, the lancet needle tip is again enclosed by the elastic material of the lancet body which thus prevents accidental injury on the needle tip.

In order to increase the stability of the elastic material it is possible to combine it with a stiff material, for example a stiff plastic material. For example the outside of the elastic material which does not come into contact with the tip of the lancet needle can be stabilized with a layer of a stiff material, for example a stiff plastic. It is also possible to manufacture the lancet body from elastic material only in the region of the lancet needle tip and to manufacture the remaining lancet body from conventional stiff plastics. In this case the elastic material and the stiff material can be glued together or joined together by an injection moulding process, for example a two component injection moulding process. The stiff material of the lancet body ensures the mechanical stability of the elastic material during the lancing process and facilitates the immobilization of the elastic part of the lancet body during the lancing process by the lancing aid. The stiff material can also be a part of the test element, for example a capillary gap test element as described in WO 99/29429.

In a further embodiment of the invention the lancet contains a lancet needle with a tip and a hollow body which surrounds at least the tip of the lancet needle, the lancet needle being movable within the hollow body in the region of its tip and the hollow body being at least partially composed of an elastic material that can be pierced by the tip of the lancet needle during the lancing process and which optionally reseals the tip of the lancet needle in the hollow body when it is retracted.

Whereas with the lancet described further above according to the first embodiment, the region of the tip of the lancet needle is completely surrounded on all sides by an elastic material and thus without any remaining hollow space around the tip to ensure sterility before use and hygienic shielding after use, in the second embodiment described above the tip of the lancet needle is surrounded by the hollow body which is closed on all sides. The areas of this hollow body which do not come into contact with the lancet needle are preferably manufactured from a stiff material and preferably an injection mouldable material. It is important for the invention that the area of the hollow body which is pierced by the lancet needle tip during the lancing process is composed of an elastic material.

During the lancing process the lancet needle is moved relative to the hollow body which represents the lancet body. The holder and drive for the lancet needle and attachment of the lancet body can be achieved by suitable constructional measures in the lancing aid as described above.

The elastic material which comprises a part of the hollow lancet body is pierced by the lancet needle tip during the lancing process and optionally reseals after the lancet needle tip is retracted into the hollow body and thus seals the hollow body. Hence the lancet needle tip is thus aseptically sealed in the hollow body immediately before use and is hygienically enclosed in it after use.

The lancet of this embodiment can, like the lancet of the alternative inventive embodiment described above, also have an additional lancet body in addition to the lancet body which encloses the tip of the lancet needle which interacts with suitable elements of a lancing device during the lancing process. In addition the lancet needle can have a special shape, for example have a head at the end opposite to the tip.

With regard to the properties of the elastic material and the joining of the elastic material with the stiff material of the lancet body the same applies as that already mentioned above with reference to the first embodiment.

The blood transfer from the wound/puncturing site of the lancet to the measuring site is achieved according to the invention by two basically different methods: On the one hand the operator of the analytical device can manually transfer the blood drop obtained after the lancing process onto the corresponding test element. However, the blood transfer is preferably achieved "automatically" without any assistance by the user of the dispos according to the invention. For this purpose the dispo can have means for sample liquid transport. These means are preferably capillary active, for example in the form of a gap or a channel in a rigid main body or absorbent matrix materials. It is also possible to combine these two basic methods for example in that the blood is firstly transported through a capillary channel, taken up by an absorbent matrix material and dispensed onto a test element.

Fleeces, papers, wicks or fabrics have proven to be particularly suitable as absorbent materials in the sense of this invention.

In a preferred embodiment the main body (lancet body) of the analytical device contains the means for sample liquid transport. This may be an absorbent wick recessed into the lancet body or preferably a formed capillary gap which is located directly next to the needle and has an inlet in the proximity of the needle outlet. As a result the dispo does not have to be laterally moved for blood collection (or only slightly). The geometry of the inlet opening is designed such that the blood drop that forms can collect there as easily as possible and has for example a funnel or notch shape. The capillary action then ensures that the required amount of blood, which can be considerably below 1 microlitre, is aspirated. By this means the blood reaches the test field and reacts there with the test chemistry to generate an analysable electrical signal or colour change. The capillary gap can be moulded into the plastic during the injection moulding or be subsequently introduced into the plastic body for example by embossing or milling.

In another preferred variant the means for sample liquid transport (e.g. a capillary gap or a wick) is not moulded into the plastic which forms the lancet body but is produced by the specific structure of the test element. For example the test element can have a structure similar to WO 99/29429 or EP-A 0 359 831.

The methods known in the prior art are used for the sensory detection of the analyte in particular of blood glucose. Photometric and electrochemical methods are preferred.

The analytical test element of the inventive analytical device can be composed of a detection film which is directly joined to the lancet body. Such detection films are known in diverse embodiments from the prior art. For example such a detection film is described in WO 99/29429. Furthermore, as already mentioned above, a complete conventional test element can be joined to the main body/lancet body of the device according to the invention. Such test elements are also known to a person skilled in the art.

The test element can be joined to the lancet body in many different ways. These include but are not limited to, glueing, welding, clipping, attachment via velcro fastening or magnets, sewing, screwing and such like. The test element is preferably glued to the lancet body for example by means of hot-melt adhesive or by means of a double-coated adhesive tape.

In general the operation of the disposables according to the invention can be described as follows:
1. The dispo is inserted into the holding device of a (blood sugar) measuring instrument and is attached there.
2. The drive mechanism of the lancing unit is tensioned and coupled to the needle thickening of the dispo.
3. When the lancing process is actuated, the needle is moved forwards and in this process emerges at high speed from the soft plastic. The entire lancing process only takes a few milliseconds.
4. After the skin has been punctured the needle is retracted again into the soft plastic (initial position). The drive is optionally disengaged.
5. After a suitable drop of blood has formed, the entire collection device is moved forward until the suction opening (e.g. capillary) contacts the drop. Alternatively the blood drop can be manually applied to the appropriate sample application zone of the test element.
6. In the variants of the disposable which have means for sample liquid transport, the suction action of these means transports the blood in the dispo to a site where a signal is generated by means of a photometric or electrochemical reaction which depends on the concentration of the blood component.

A disposable according to the invention can in principle be manufactured by the following simple steps:
(1) Injection moulding the main body including embedding the lancet needle (optionally with generation of the "needle head" i.e. a thickening that can be engaged by a lancing instrument)
(2) sheathing the needle tip with soft plastic
(3) sterilizing the "crude disposables" (which are essentially composed of the lancet optionally together with a capillary channel in the lancet body) for example by means of gamma radiation
(4) test assembly i.e. connecting the test element with the main body.

Preferably the "crude dispos" as well as the test elements can be present as a tape material which is separated into the individual dispos after the test assembly for example by cutting or punching. Irrespective of whether the disposables according to the invention are manufactured as rolls or tape material in a continuous process or batch-wise or individually, it is important that the lancet and test element are not joined together until after the lancet needle has been sterilized. A sterilization of the disposables after final assembly could result in damage to sensitive chemical or biological substances in the test field. This can be avoided by the process according to the invention.

Finally a subject matter of the invention is the use of an elastic material as a component of a lancet of an analytical device where the elastic material maintains the sterility of at least the tip of a lancet needle in the unused state. In a preferred embodiment the elastic material can also be used to hygienically shield at least the tip of the lancet needle in the used state.

The use according to the invention of an elastic material to shield the tip of the lancet needle ensures the sterility of an unused lancet needle tip and optionally hygienically shields the used lancet needle tip.

The lancet needle tip can be sterilized in the unused state by suitable measures such as for example gamma radiation. Once sterilized the lancet needle tips remain sterilized by the corresponding lancet body which includes an elastic material. In contrast to the prior art where no elastic materials for shielding lancet needle tips have been described, the use of the elastic material according to the invention also enables the hygienic screening or shielding of the used lancet needle tip. The use of the elastic material allows resealing of a channel which may be present for a brief time through which the lancet needle can pass for the purposes of lancing after the lancet needle has been retracted i.e. after completion of the lancing process. Hence contaminants, in particular germs and infectious material which may adhere to the lancet needle tip after the lancing process cannot reach the environment or only to a limited extent. This is of particular advantage for disposable lancets which are individually disposed of after use. This property is, however, of outstanding importance for sets of lancets and lancet magazines in which used lancets are stored next to unused lancets which can then be disposed of as a whole.

The invention has the following advantages:
The tip of the lancet needle is shielded germ-tight in the unused state in all embodiments i.e. germs cannot reach the lancet needle tip until immediately before using the lancet. After suitable sterilization the lancet tips remain sterile for a long period.
The sterility of the lancet needle is also ensured in the subsequent manufacturing steps such as the joining of lancet and test element. In this process the sensitive needle tip is protected from mechanical influence (bending etc.).
In all embodiments the tip of the lancet needle can be hygienically screened in the used state. An accidental contamination of the surroundings (user, objects, other lancets) is substantially excluded.
The user of disposables according to the invention is protected from accidental injury on a used lancet needle. The same of course also applies to other persons than the actual user.
The disposables according to the invention can be manufactured cost-effectively in large numbers using conventional injection moulding processes.
The disposables according to the invention can be miniaturized to a substantial degree and are therefore suitable for use in compact automated systems.
All previously known variants of test strips and sensors can be used as analytical test elements.

The invention is further elucidated by the following figures:
FIG. 1 shows schematically a first preferred embodiment of the analytical device according to the invention in several views.
FIG. 2 shows schematically a second preferred embodiment of the analytical device according to the invention in several views.
FIG. 3 shows schematically a third preferred embodiment of the analytical device according to the invention in several views.
FIG. 4 shows schematically a fourth preferred embodiment of the analytical device according to the invention in several views.
FIG. 5 shows schematically a fifth preferred embodiment of the analytical device according to the invention in several views.
FIG. 6 shows schematically the manufacture of analytical devices according to FIG. 2 from tape material.

Although only test elements that can be evaluated optically are shown in each of the individual figures, this should not be limiting to the subject matter of the present invention. Rather it is obvious to a person skilled in the art that the detection reaction of the test element can be monitored by any method. In addition to optical methods (such as reflection photometry, absorption measurement or fluorescence measurement) in particular electrochemical methods are preferred (such as potentiometry, amperometry, voltametry, coulometry for example).

The figures and letters in the figures denote:
1 analytical device (disposable, dispo)
2 lancet
3 lancet needle
4 lancet body
5 plastic part of the lancet body
6 part of the lancet body made of elastic material
7 capillary gap
8 thickening of the needle end
9 test element
10 test field
11 sealing foil
12 thickening in the middle of the needle
13 lancet tape/belt
14 test element tape/belt FIG. 1 shows schematically a preferred embodiment of the analytical device in several detail FIGS. (1A-1E).

FIG. 1A firstly shows the lancet (2). It contains a lancet needle (3) which is embedded in a lancet body (4). The lancet body (4) is composed of a hard plastic part (5) and a part made of elastic material (6). A capillary gap (7) is worked into the hard plastic part (5) of the lancet body (4) and is used to transport the sample liquid.

A thickening (8) is attached to the rear end of the lancet needle (3) and enables the lancet needle to be easily gripped in the lancing aid or in the lancing instrument.

FIG. 1B shows the final analytical device (1). A strip-shaped test element (9) which contains a test field (10) is attached to the hard plastic part (5) of the lancet body (4). The test field is accessible for sample liquid through the capillary gap (7).

FIG. 1C shows a perspective view of the underside of the analytical device (1). In this view it is clear that the hard plastic part (5) of the lancet body (4) only touches and holds the lancet needle (3) in the area of two bars. Furthermore the dashed lines indicate how the tip of the lancet needle (3) is embedded in the elastic material (6) of the lancet body.

FIG. 1D shows a longitudinal section through the analytical device (1).

FIG. 1E shows a front view of the analytical device (1).

The drawings (2A-2E) of FIG. 2 show another preferred embodiment of the analytical device according to the invention.

In FIG. 2A the lancet (2) of the analytical device (1) is first shown in perspective from above. The lancet (2) is composed of a lancet needle (3) which is embedded in a lancet body (4). This is composed of a hard plastic part (5) and a part made of an elastic material (6). In addition a thickening (8) is attached to the rear end of the lancet needle (3) which is used to grip the lancet needle (3) by a lancing instrument.

In contrast to FIG. 1 the analytical device in FIG. 2 does not have a capillary gap in the lancet body (4) but as part of the test element (9).

FIG. 2B shows the final assembled analytical device (1) in which a test element (9) is attached to the lancet body (4). This test element contains a capillary gap (7) which makes the test field (10) accessible to a blood sample.

FIG. 2C shows a perspective view of the analytical device (1) according to FIG. 2B from below. As in FIG. 1C, FIG. 2C makes it clear that the lancet needle (3) is only connected to the hard plastic part (5) of the lancet body (4) by bars. The needle tip of the lancet needle (3) is completely embedded in the elastic material (6) of the lancet body.

FIG. 2D represents a longitudinal section through the analytical device (1) of FIG. 2B. FIG. 2E shows a corresponding front view of the analytical device (1) of FIG. 2B. FIGS. 2D and 2E make it clear that the capillary gap (7) is part of the test element (9).

FIG. 3 shows another preferred embodiment of the analytical device (1) of the invention in several detailed drawings (3A-3E).

The embodiment of FIG. 3 contains a capillary gap (7) as part of the hard plastic part (5) of the lancet body (4) similar to the embodiment of FIG. 1. Only the position of the capillary gap (7) and the position of the test element (9) differ from the embodiment of FIG. 1. Whereas in the embodiment of FIG. 1 the test element (9) and capillary gap (7) are arranged on one of the large boundary surfaces of the lancet body (4), these elements are arranged laterally on one of the narrow boundary surfaces of the lancet body (4) in the embodiment of FIG. 3. Otherwise the function and structure of the embodiment of FIG. 3 essentially corresponds to that described in FIG. 1. In this connection FIGS. 3A to 3E correspond to FIGS. 1A to 1E.

Another preferred embodiment of the analytical device (1) according to the invention is shown in several detailed drawings (FIGS. 4A-4F) in FIG. 4. Whereas in the embodiments according to FIG. 1 to FIG. 3 the capillary gap (7) was either part of the hard plastic part (5) of the lancet body (4) or part of the test element (9), the capillary gap (7) in the embodiment of FIG. 4 is partially disposed in the elastic material (6) of the lancet body (4) and partially in the test element (9). As shown in particular in FIG. 4D the capillary gap (7) can be divided into three partial regions (7, 7A and 7B). These are in contact with one another in such a manner that sample liquid transport is possible.

As in the embodiments of FIGS. 1 to 3, the embodiment of FIG. 4 is composed of a lancet (2) which contains a lancet needle (3) which is partially surrounded by a lancet body (4). In this case the lancet body (4) is composed of a hard plastic part (5) and an elastic material (6) which in particular surrounds the lancet needle tip (cf. FIG. 4A). A thickening (8) is attached to the lancet needle at the rear end of the lancet body (3) which in turn is designed to enable a lancing device to grip the needle (3).

As shown in FIGS. 4B and 4C, a test element (9) which contains a test field (10) is attached to the lancet body (4). As already described the test field (10) is accessible to the sample liquid via a system of capillary channels (7, 7A, 7B).

The outlet opening of the lancet needle (3) is closed by a sealing foil (11) in this embodiment. When the lancet is used the sealing foil (11) can either be pierced by the lancet needle (3) or the sealing foil (11) is removed manually before use.

FIG. 4E shows a front view of the outlet opening of the lancet of the analytical device (1).

FIG. 4F shows an enlarged view of the detail labelled X in the front view of FIG. 4E. This view shows especially that four capillary channels (7) which enable sample transport to the test element (9) are present in the elastic material (6) of the lancet body (4).

A thickening (8) is provided in the rear of the lancet needle (3) in embodiments of FIGS. 1 to 4 which is of major importance for the lancing movement. This thickening (8) is designed such that it can be coupled to a lancing drive. In this case the drive carries out the forwards and backwards movement of the needle (3). Alternatively a drive coupling is also conceivable in which a plunger carries out the forward movement. It is then moved back by a spring which is pressed together during the forward movement and then subsequently relaxes. The thickening (8) on the needle (3) is important for this as one of the contact points for the spring. This spring can either be a component of the disposable or a component of the instrument or of a cassette or a magazine. The thickening (8) can for example be an attachable plastic or metal part. The needle (3) can also be mechanically deformed (squeezing, bending) to produce a thickening (8).

Another embodiment of the invention is shown in several detailed drawings (5A-5D) of FIG. 5. In this embodiment the thickening (11) of the lancet needle (3) is not at the rear end of the lancet needle (3), but rather in the region of the middle of the needle. In this case the thickening is located inside the lancet body (4). In this case an appropriate drive mechanism can only act laterally on the disposable. An advantage of this solution is that disposables are particularly compact and robust.

Otherwise the analytical device (1) corresponds essentially to the embodiment of FIG. 2.

Of course it is also possible to combine an embodiment of FIG. 1 i.e. an embodiment in which the capillary gap (7) is part of the lancet body (4) with a thickening (12) in the middle of the needle.

FIG. 5A shows a view of the analytical device (1) from below. FIG. 5B shows a sectional view through the longitudinal axis of the analytical device (1). FIG. 5C shows a perspective view of the underside of the analytical device (1) in which the lancet needle (3) is in a position in which it is before or after the lancing process. The tip of the lancet needle is embedded in the elastic material (6) of the lancet body. In FIG. 5D—which for the sake of clarity is shown without a test element (9) and elastic material (6)—the lancet (2) is in the position in which the lancet needle (3) is present during the lancing process. The lancet needle tip protrudes from the contours of the lancet body (4).

FIG. 6 is a greatly simplified schematic representation of how analytical devices (1) according to FIG. 2 are manufactured from tape material. In area A lancets (12) which are assembled to form a tape or belt (13) and test elements (9) are assembled to form a tape or belt (14). Two tapes are combined in area B and the test element tape (14) is glued to the lancet tape (13). Finally in area C the combined tapes are cut into individual analytical devices (1) for example by cutting off the terminal device (1).

The invention claimed is:

1. An analytical device comprising:
   i) a lancet comprising
   a lancet needle with a tip and
   a lancet body which completely surrounds the lancet needle at least in the area of the tip,
   the lancet needle being movable relative to the lancet body and the lancet body comprising, at least in the area of the tip of the lancet needle, an elastic material in which the tip of the lancet needle is embedded therein without a hollow space remaining, both before and after the tip penetrates the elastic material to form an incision in tissue, wherein the elastic material is an injection moldable material, and
   ii) an analytical test element, the analytical test element being permanently connected to the lancet body.

2. An analytical device as claimed in claim 1, wherein the elastic material is a thermoplastic elastomer.

3. An analytical device as claimed in claim 1, wherein the lancet body has means for sample liquid transport.

4. An analytical device as claimed in claim 1, wherein the test element has means for sample liquid transport.

5. An analytical device as claimed in claim 1, wherein the lancet includes one of a capillary gap, a capillary channel or a wick or a bar made of an absorbent material.

6. An analytical device as claimed in claim 1, wherein the lancet body has a sample application site which is directly adjacent to an outlet opening of the tip of the lancet needle.

7. A tissue penetrating system, comprising:
   a plurality of penetrating members each having a sharpened distal tip;
   a penetrating member driver coupled to the plurality of penetrating members; and
   a plurality of cartridges each housing a penetrating member and configured so that the penetrating member driver engages each of the penetrating members sequentially, the cartridge including an injection moldable material, said sharpened distal tip embedded in said injection moldable material of said cartridge without a hollow space remaining, said sharpened distal tip being configured to pierce through said cartridge to form an incision in tissue when said penetrating member driver is actuated, said cartridge further configured to seal said sharpened distal tip therein after said distal tip forms the incision in tissue, each cartridge defines a capillary chamber, each cartridge including an analyte detecting member coupled to said capillary chamber, the analyte detecting member being configured to determine a concentration of an analyte in a body fluid using a sample of less than 1 μL of a body fluid disposed in the capillary chamber.

8. The system of claim 7, wherein each cartridge has a plurality of seals positioned so that the sharpened distal tip remains in a sterile environment before launch of a penetrating member, the plurality of modules coupled together in an array.

9. The system of claim 7, further comprising:
   a penetrating member sensor coupled to the plurality of penetrating members, the penetrating member sensor configured to provide information relative to a depth of penetration of a penetrating member through a skin surface.

10. The system of claim 7, further comprising:
    a user interface configured to relay at least one of, skin penetrating performance or a skin penetrating setting.

11. The system of claim 7, further comprising:
    a human interface providing at least one output.

12. A body fluid sampling system for use on a tissue site, the system comprising:
    a drive force generator;
    a penetrating member with a penetrating member tip, said penetrating member operatively coupled to said force generator, said force generator moving said member along a path out of a housing having a penetrating member exit, into said tissue site, stopping in said tissue site, and withdrawing out of said tissue site;
    a penetrating member body including an injection moldable material which completely surrounds and contacts said penetrating member tip without a hollow space remaining, said penetrating member body further defining a capillary gap configured to collect fluid from a wound created by said penetrating member tip;
    a skin stabilizer device suitable for stretching a surface of a tissue site, said skin stabilizer device at least partially surrounding the penetrating member exit;
    an analyte detecting member positioned to receive fluid from a wound created by said penetrating member tip and delivered by said capillary gap, said analyte detecting member configured to determine a concentration of an analyte in the fluid using a sample of less than 1 mL of the fluid; and
    a user interface configured to relay at least one of, penetrating member performance or a penetrating member setting.

13. A body fluid sampling system for use on a tissue site, the system comprising:
    a drive force generator;
    a penetrating member having a penetrating member tip, said penetrating member operatively coupled to said force generator, said force generator moving said member along a path out of a housing having a penetrating member exit, into said tissue site, stopping in said tissue site, and withdrawing out of said tissue site;
    a penetrating member body including an injection moldable material which completely surrounds and contacts the penetrating member tip without a hollow space remaining, said penetrating member body further defining a capillary gap configured to collect fluid from a wound created by said penetrating member tip;
    a skin stabilizer device suitable for stretching a surface of a tissue site, said skin stabilizer device at least partially surrounding the penetrating member exit;
    an analyte detecting member positioned to receive fluid from a wound delivered by said capillary gap, said analyte detecting member configured to determine a concentration of an analyte in the fluid using a sample of less than 1 mL of the fluid; and
    a human interface providing at least one output.

14. A body fluid sampling system for use on a tissue site, the system comprising:
    a drive force generator;
    a penetrating member having a penetrating member tip, said penetrating member operatively coupled to said force generator, said force generator moving said member along a path out of a housing having a penetrating member exit, into said tissue site, stopping in said tissue site, and withdrawing out of said tissue site;
    a penetrating member body including an injection moldable material which completely embeds the penetrating member tip therein without a hollow space remaining, said penetrating member body further defining a capillary gap configured to collect fluid from a wound created by said penetrating member tip;
an analyte detecting member positioned to receive fluid from a wound delivered by said capillary gap, said analyte detecting member configured to determine a concentration of an analyte in the fluid using a sample of less than 1 mL of the fluid; and
a user interface configured to relay at least one of, penetrating member performance or a penetrating member setting.

15. A body fluid sampling system for use on a tissue site, the system comprising:
a drive force generator;
a plurality of penetrating members operatively coupled to said force generator, said force generator moving each of said members along a path out of a housing having a penetrating member exit, into said tissue site, stopping in said tissue site, and withdrawing out of said tissue site, each of the penetrating members having a penetrating member tip;
a plurality of penetrating member bodies that cover said plurality of penetrating member tips, each of said penetrating member bodies includes an injection moldable material that completely surrounds and contacts a corresponding one of said penetrating member tips without a hollow space remaining, each of said penetrating member bodies further defining a capillary channel configured to collect fluid from a wound created by said penetrating member tip;
a flexible support member coupling said penetrating members to define a linear array, said support member being movable and configured to move each of said penetrating members to a launch position associated with said force generator; and
an analyte detection member positioned to receive fluid from said capillary channel, said detection member configured to determine a concentration of an analyte in the fluid using a sample of less than 1 mL of the fluid.

16. A body fluid sampling system for use on a tissue site, the system comprising:
a drive force generator;
a penetrating member having a penetrating member tip, said penetrating member operatively coupled to said force generator, said force generator moving said member along a path out of a housing having a penetrating member exit, into said tissue site, stopping in said tissue site, and withdrawing out of said tissue site;
a penetrating member body configured to store the penetrating member, said penetrating member body including an injection moldable material that embeds said penetrating member tip therein without a hollow space remaining, said penetrating member body further defining a capillary channel configured to collect fluid from a wound created by said penetrating member;
an analyte detection member positioned to receive fluid from the capillary channel, said detection member configured to determine a concentration of an analyte in the fluid using a sample of less than 1 mL of the fluid; and
a tissue stabilizing member associated with said housing and positioned to at least partially surround an impact location of the penetrating member on the tissue site.

17. A body fluid sampling system for use on a tissue site, the system comprising:
a drive force generator;
a plurality of penetrating members operatively coupled to said force generator, said force generator moving each of said members along a path out of a housing having a penetrating member exit, into said tissue site, stopping in said tissue site, and withdrawing out of said tissue site, wherein each of said plurality of penetrating members has a penetrating member tip;
a plurality of penetrating member bodies configured to store said plurality of penetrating members, each of said plurality of penetrating member bodies includes an injection moldable material that embeds said plurality of penetrating member tips therein without a hollow space remaining, each of said penetrating member bodies further defining a capillary channel configured to collect fluid from a wound created by said penetrating member;
a flexible support member coupling said penetrating members to define a linear array, said support member being movable and configured to move each of said penetrating members to a launch position associated with said force generator; and
an analyte detection member positioned to receive fluid from said capillary channel.

18. The system of claim 17, wherein said detection member configured to determine a concentration of an analyte in the fluid using a sample of less than 1 µL of the fluid.

19. A skin penetrating system, comprising:
a housing member having an injection moldable material;
a penetrating member having a penetrating tip, the penetrating tip being embedded in the injection moldable material before use without a hollow space remaining, the penetrating tip being configured to pierce through the injection moldable material to form an incision in tissue, the injection moldable material configured to embed the penetrating tip therein after the penetrating tip has formed the incision in tissue; and
an analyte detecting member coupled to a sample chamber, the analyte detecting member being configured to determine a concentration of an analyte in a body fluid using a sample of less than 1 µL of a body fluid disposed in the sample chamber.

* * * * *